United States Patent
Chan et al.

(10) Patent No.: US 6,224,880 B1
(45) Date of Patent: May 1, 2001

(54) **IMMUNIZATION AGAINST *STREPTOCOCCUS PNEUMONIAE* USING CONJUGATED AND UNCONJUGATED PNEUMOCCOCAL POLYSACCHARIDE VACCINES**

(75) Inventors: Christina Y. Chan, Lansdale, PA (US); Jerald C. Sadoff, Washington, DC (US)

(73) Assignee: Merck & Co., Inc., Rahway, NJ (US)

( * ) Notice: Subject to any disclaimer, the term of this patent is extended or adjusted under 35 U.S.C. 154(b) by 0 days.

(21) Appl. No.: 09/145,661

(22) Filed: Sep. 2, 1998

Related U.S. Application Data
(60) Provisional application No. 60/059,872, filed on Sep. 24, 1997.

(51) Int. Cl.$^7$ .................................................. A61K 39/09
(52) U.S. Cl. .................. 424/244.1; 424/9.2; 424/193.1; 424/197.11; 424/203.1; 435/7.32; 530/403
(58) Field of Search ................... 424/9.2, 193.1, 424/244.1, 197.11, 203.1; 435/7.32; 530/403, 404

(56) References Cited

U.S. PATENT DOCUMENTS

| | | | |
|---|---|---|---|
| 4,673,574 | 6/1987 | Anderson | 424/92 |
| 4,686,102 | 8/1987 | Ritchey et al. | 424/92 |
| 4,695,624 | 9/1987 | Marburg et al. | 530/395 |
| 4,882,317 | 11/1989 | Marburg et al. | 514/54 |
| 5,371,197 | 12/1994 | Marburg et al. | 530/404 |
| 5,445,817 | 8/1995 | Schmeerson et al. | 424/194.1 |
| 5,623,057 | 4/1997 | Marburg et al. | 530/404 |

FOREIGN PATENT DOCUMENTS

| | | |
|---|---|---|
| 0 002 404 | 11/1976 | (EP) . |
| 0 497 524 A2 | 1/1992 | (EP) . |
| WO 94/04195 | 3/1994 | (WO) . |

OTHER PUBLICATIONS

Fedson, "Pneumococcal Vaccine", Vaccines, (Plotkin and Mortimer eds.), pp. 271–299.

Ahomkhai, et al., "Failure of Pneumococcal Vaccine in Children with Sickle–Cell Disease", The New England Journal of Medicine, pp. 26–27, Jul. 5, 1979.

Peter, et al., "Pneumococcal Vaccine", Pediatrics in Review, vol. 17, No. 10, pp. 335–341, Oct. 1996.

Anderson, et al., "Interchangeability of Conjugated *Haemophilus influenzae* Type b Vaccines in Infants", JAMA, Mar. 15, 1995, vol. 273, No. 11, pp. 849–853.

Stein, "Thymus–Imdependent and Thymus–Dependent Responses to Polysaccharide Antigens", J. Infectious Dis., 165 (Suppl. 1) S49–S52.

Koskela, et al., "Serum antibody response to pneumococcal otitis media", Pediatric Infectious Disease, vol. 1, No. 4, pp. 245–252, 1982.

Schiffman, et al., "A Radioimmunoassay For Immunologic Phenomena in Pneumococcal Disease . . . ", J. Immunol. Methods, 33, pp. 133–144. 1980.

Sell, et al., "Clinical Studies of Pneumococcal Vaccines in Infants . . . ", Reviews of Infectious Diseases, vol. 3 Supplement, pp. S97–S107, Mar.–Apr. 1981.

Anderson, et al., "Immunogenicity of heptavalent pneumococcal conjugate vaccine in infants", The Journal of Pediatrics, pp. 649–653, May 1996.

Douglas, et al., "Antibody Response to Pneumococcal Vaccination in Children Younger than Five Years of Age", The J. of Infect. Dis., vol. 148, No. 1, pp. 131–137, Jul. 1983.

Prober, et al., "Immunologic Responses of Children to Serious Infections with *Streptococcus Pneumoniae*", J. of Infect. Dis., vol. 148, No. 3, pp. 427–435, Sep. 1983.

Koskela, et al., "Comparison of ELISA and RIA for measurement of pneumoccal antibodies before and after vaccination . . . ", J. Clin. Pathol., vol. 34, pp. 93–98, 1981.

Kojima, et al., Quantitation of IgG Subclass Antibodies to Pneumococcal Capsular Polysaccharides by ELISA . . . , J. Exp. Med., vol. 161, pp. 209–215, 1991.

Pp. 1768–1770 of the 1991 Edition of the Physician's Desk Reference (Medical Economics, Montvale, NJ).

Kayhty, et al., "High Antibody Responses to Booster Doses os Either *Haemophilus Influnzae* Capsular . . . ", J. of Infect. Dis., 165 (Suppl. 1) S165–S166.

Granoff, et al., "Induction of Immunologic Memory in Infants Primed with Haemophilus . . . ", J. of Infect. Dis., vol. 168, pp. 663–671.

Kurikka, et al., "Neonatal Immunization: Response to *Haemophilus influenzae* Type b–Tetanus . . . ", Pediatrics, vol. 95, No. 6, Jun. 1995, pp. 815–822.

Primary Examiner—Jeffrey Stucker
Assistant Examiner—Ulrike Winkler
(74) Attorney, Agent, or Firm—Joseph A. Coppola; Jack L. Tribble

(57) ABSTRACT

A method of immunizing against disease caused by *Streptococcus pneumoniae* is provided in which children are immunized at age 2 and again at age 4 months with a conjugated pneumococcal polysaccharide vaccine. These immunizations are followed by an immunization at 6 months with an unconjugated pneumococcal polysaccharide vaccine. Optionally, a fourth immunization at 12 months with unconjugated pneumococcal polysaccharide vaccine is given.

15 Claims, No Drawings

IMMUNIZATION AGAINST *STREPTOCOCCUS PNEUMONIAE* USING CONJUGATED AND UNCONJUGATED PNEUMOCCOCAL POLYSACCHARIDE VACCINES

CROSS-REFERENCE TO RELATED APPLICATIONS

This application claims the benefit of U.S. Provisional Application No. 60/059,872, filed Sep. 24, 1997, the contents of which are incorporated herein by reference in their entirety.

STATEMENT REGARDING FEDERALLY-SPONSORED R&D

Not applicable.

REFERENCE TO MICROFICHE APPENDIX

Not applicable.

FIELD OF THE INVENTION

This invention relates to methods of immufiing children against *Streptococcus pneumoniae* that comprise immunizations with a conjugated pneumoccocal polysaccharide vaccine at the ages of 2 and 4 months followed by immunization with an unconjugated pneumococcal polysaccharide vaccine at the age of 6 months. Optionally, these methods are followed by a further immunization with unconjugated pneumococcal polysaccharide vaccine at the age of 12 months.

BACKGROUND OF THE INVENTION

*Streptococcus pneumoniae* is the cause of a variety of common respiratory and systemic infections of infancy and early childhood such as pneumonia, otitis media, and meningitis. Such pneumoccocal infections can range in severity from asymptomatic to life threatening. The emergence of strains of *S. pneumoniae* that are resistant to a variety of antibiotics has resulted in a great need for improved methods of vaccination against *S. pneumoniae*. This need is especially acute in the case of children between the ages of 6 months and 24 months, in whom disease caused by *S. pneumoniae* can be especially severe.

*S. pneumoniae* is a gram-positive microorganism containing a cell wall surrounded by a polysaccharide capsule. The polysaccharide capsule is the primary virulence factor of *S. pneumoniae* and provides the basis for type-specific identification of approximately 90 different serotypes. Capsular polysaccharides stimulate the production of type-specific antibodies that can confer protection against *S. pneumoniae* (Fedson, 1988, in *Vaccines* (Plotkin and Mortimer, eds.), E.B. Saunders Co., Philadelphia, pp. 271–299 [Fedson]; Prober et al., 1983, J. Infect. Dis. 148:427–435; Koskela et al., 1982, Pediatr. Infect. Dis. 1:245–252). It is generally accepted in the art that the higher the level of a particular type-specific antibody, the greater the level of protection against that particular serotype of *S. pneumnoniae*. Thus, in the absence of human efficacy trials, the measurement of antibody levels following vaccination has come to be the art-recognized method of evaluating the effectiveness of new vaccines or new methods of vaccination. See, e.g., Fedson, at page 279: "Clinical and experimental observations have firmly established the association between the presence of type-specific serum antibody and the protection against infection by homologous pneumococcal organisms." See, also, Schiffman et al., 1980, J. Immunol. Meth. 33:133–144 ("Antibodies to pneumococcal capsular polysaccharides are determined for the following reasons: (1) to ascertain the immune response to a vaccine in order to assess protection against pneumococcal types in the vaccine . . . "). Accordingly, there has been much effort expended in attempts to develop vaccines that will raise the level of type-specific antibodies to *S. pneumoniae* in vaccinees.

Currently licensed vaccines against *S. pneumoniae* are based on a combination of pneumococcal polysaccharides that are present in unconjugated form. For example, PNEUMOVAX®23, produced by Merck Sharp & Dohme, West Point, Pa., consists of a combination of 23 different purified pneumococcal polysaccharides. PNU-IMUNE®23 is an unconjugated vaccine produced by Lederle Laboratories, Pearl River, N.Y., containing the same 23 capsular polysaccharide antigens as is contained in PNEUMOVAX®23.

While such unconjugated pneumococcal polysaccharide vaccines are highly effective in many patient populations, they are often not very effective in children younger than two years of age (Douglas et al., 1983, J. Infect. Dis. 148:131–137; Ahonkai et al., 1979, New Eng. J. Med. 301:26–27; Sell et al., 1981, Rev. Infect. Dis. 3:S97-S107). This is probably due to the immaturity of T cell independent humoral immune responses at that age. The lack of efficacy of unconjugated pneumococcal polysaccharide vaccines in children younger than two years old has led some researchers to conclude with respect to unconjugated vaccines that "The immunogenicity of polysaccharide pneumococcal vaccine . . . is absent or minimal for most of the capsular polysaccharides in children younger than 2 years of age. Hence, vaccination is not indicated until 2 years of age." (Peter & Klein, 1996, Pediatrics in Review 17:335–341).

As a result of the lack of immunogenicity of unconjugated pneumococcal polysaccharide vaccines in children less than two years old, alternative vaccines have been sought. Some pneumococcal vaccines that are currently under development or in clinical testing utilize pneumococcal polysaccharides that have been conjugated to protein carriers. For example, PCV is a heptavalent conjugated pneumococcal polysaccharide vaccine produced by Merck Sharp & Dohme, West Point, Pa. PCV consists of seven serotypes of pneumococcal polysaccharides (4, 6B, 9V, 14, 18C, 19F, and 23F according to the Danish nomenclature) that have been conjugated to the outer membrane protein complex of *Neisseria meningitidis*. One hope for such conjugated pneumococcal polysaccharide vaccines is that they will be able to induce a better immune response in young children because, since these conjugated vaccines contain carrier proteins, they will be able to stimulate T cell dependent pathways of humoral immunity while unconjugated polysaccharide vaccines may be restricted to stimulating antibody production by T cell independent pathways. T cell dependent pathways of humoral immunity are not age-dependent and exist at birth.

Evidence that conjugated pneumococcal polysaccharide vaccines may be useful in very young children has been presented. Some investigators have used four doses of conjugated vaccine at 2, 4, 6, and 12 months. Other approaches utilized unconjugated instead of conjugated vaccine at age 12 months. For example, Anderson et al., 1996, J. Pediatrics 128:649–653 (Anderson) vaccinated children at 2, 4, and 6 months of age with a conjugated pneumococcal polysaccharide vaccine (PCV) and followed with a single dose of unconjugated polysaccharide vaccine (PNEUMOVAX®23) at age 12 or 15 months. This vaccination schedule resulted in a significant increase in antibody titers to all seven serotypes in the conjugated vaccine. However, an effective vaccination regimen that makes use of unconjugated vaccine at the age of six months or younger has not been reported. Accordingly, despite such studies as that of Anderson, there remains a great need for developing even more highly effective methods of immunizing young children against *S. pneumoniae* utilizing conjugated and unconjugated pneumococcal polysaccharide vaccines.

SUMMARY OF THE INVENTION

The present invention provides methods of immunizing children against pneumococcal disease that comprise two immunizations with a conjugated pneumoccocal polysaccharide vaccine prior to the age of 6 months followed by one immunization with an unconjugated pneumococcal polysaccharide vaccine at the age of 6 months. The present invention provides for the production of antibody titers in the immunized children to the *Streptococcus pneumoniae* serotypes found in the conjugated vaccine that exceed the titers produced by prior art methods.

BRIEF DESCRIPTION OF THE DRAWINGS

Not applicable.

DETAILED DESCRIPTION OF THE INVENTION

For the purposes of this invention, "pneumococcuse" or "pneumococcal" refers to *Streptococcus pneumoniae*. "Pneumococcal disease" refers to disease caused by *Streptococcus pneumoniae*. "Pneumococcal vaccine" and "pneumococcal polysaccharide vaccine" are used interchangeably.

This invention provides a novel method of combining immunizations using conjugated and unconjugated pneumococcal polysaccharide vaccines. Due to the low level of immunogenicity provided by unconjugated pneumococcal vaccines in children, especially those under 6 months of age, prior art methods of immunizing against pneumococcal disease had employed vaccinations using conjugated vaccine at ages 6 months and younger. These priming immunizations were followed with booster immunizations using conjugated, and in one case unconjugated, vaccine at older ages, e.g., 12 months. Such a regimen is described in Anderson et al., 1996, J. Pediatrics 128:649–653 (Anderson). Anderson utilized priming immunizations at 2, 4, and 6 months with conjugated vaccine and a booster immunization at 12 or 15 months with uncowjugated vaccine.

The present inventors have discovered that an immunization with unconjugated pneumococcal polysaccharide vaccine may be given at an age as low as 6 months if such an immunization has been preceded by two immunizations with conjugated vaccine given prior to age 6 months. Thus, the present invention provides a method of vaccinating children against *Streptococcus pneumoniae* which comprises:

(a) immunizing with a conjugated pneumococcal vaccine at the age of about 2 months;

(b) further immunizing with a conjugated pneumococcal vaccine at the age of about 4 months; and (c) further immunizing with an unconjugated pneumococcal vaccine at the age of about 6 months.

The present inventors have discovered that the above-described method produces superior results when compared to a method which involves immuning children at 2, 4, and 6 months with conjugated vaccine only (i.e., no immunization with unconjugated vaccine at or before age 6 months), as in Anderson.

It will be recognized by those of skill in the art that it is not necessary that the immunizations of steps (a)–(c) in the above-described method be given at precisely 2, 4, and 6 months. Thus, the word "about" in the above-described method signifies that the immunizations may be given up to one day, two days, three days, four days, five days, six days, one week, or even two weeks, either sooner or later that the indicated 2, 4, and 6 month dates.

Of course, the immunizations may be given precisely at the indicated dates and therefore the present invention also includes a method of vaccinating children against *Streptococcus pneumoniae* which comprises:

(a) immunizing with a conjugated pneumococcal vaccine at the age of 2 months;

(b) further immunizing with a conjugated pneumococcal vaccine at the age of 4 months; and (c) further immunizing with an unconjugated pneumococcal vaccine at the age of 6 months.

In a particular embodiment of the present invention, a second dose of unconjugated vaccine is provided at age 12 months. An example of such an embodiment comprises:

(a) immunizing with a conjugated pneumococcal vaccine at the age of 2 months;

(b) further immunizing with a conjugated pneumococcal vaccine at the age of 4 months;

(c) further immunizing with an unconjugated pneumococcal vaccine at the age of 6 months; and (d) further immunizing with an unconjugated pneumococcal vaccine at the age of 12 months.

It will be recognized by those skilled in the art that, just as it is not necessary that the immunizations at the ages of 2, 4, and 6 months be given at precisely those times, it is not necessary that the immunization at 12 months be given precisely at 12 months. In the case of the second immunization with unconjugated vaccine, there is great leeway in exactly when this second immunization with unconjugated vaccine is given. Accordingly, the present invention also includes a method of vaccinating children against *Streptococcus pneumoniae* which comprises:

(a) immunizing with a conjugated pneumococcal vaccine at the age of 2 months;

(b) further immunizing with a conjugated pneumococcal vaccine at the age of 4 months;

(c) further immunizing with an unconjugated pneumocoa vaccine at the age of 6 months; and (d) further immunizing with an unconjugated pneumococcal vaccine at the age of 12, 13, 14, 15, 16, 17, or 18 months.

In a particular embodiment, a non-pneumococcal vaccine is provided concurrently with one or more of the pneumococcal vaccines in steps (a)–(c) of the methods described above. Examples of non-pneumococcal vaccines are TETRAMUNE®, RECOMBIVAX HB®, and ORIMUNE®. TETRAMUNE® is a vaccine produced by Lederle Laboratories, Pearl River, N.Y., that contains diphtheria toxoid, tetanus toxoid, Haemophilus b polysaccharide, and CRM 197 protein. RECOMBIVAX HB® is a vaccine produced by Merck Sharp & Dohme, West Point, Pa., directed to hepatitis B virus. ORIMUNE® is an oral polio vaccine.

In a particular embodiment of the present invention, the conjugated vaccine is PCV.

In another embodiment, the conjugated vaccine comprises polysaccharides of serotypes 4, 6B, 9V, 14, 18C, 19F, and 23F according to the Danish nomenclature.

In another embodiment, the conjugated vaccine comprises polysaccharides of serotypes 4, 6B, 9V, 14, 18C, 19F, and 23F according to the Danish nomenclature individually conjugated to the outer membrane protein complex of *Neisseria meningitidis*.

In another embodiment, the conjugated vaccine comprises polysaccharides of serotypes 1, 3, 5, 4, 6B, 7F, 9V, 14, 18C, 19F, and 23F according to the Danish nomenclature.

In another embodiment, the conjugated vaccine comprises polysaccharides of serotypes 1, 3, 5, 4, 6B, 7F, 9V, 14, 18C, 19F, and 23F according to the Danish nomenclature individually conjugated to the outer membrane protein complex of *Neisseria meningitidis*.

In another embodiment, the conjugated vaccine comprises polysaccharides of serotypes 4, 6B, 9V, 14, 18C, 19F and 23F conjugated to the non-toxic CRM197 variant of diptheria toxin.

In another embodiment, the unconjugated vaccine is PNEUMOVAX®23.

In another embodiment, the unconjugated vaccine comprises polysaccharides of serotypes 1, 2, 3, 4, 5, 6B, 7F, 8,. 9N, 9V, 10A, 11A, 12F, 14, 15B, 17F, 18C, 19A, 19F, 20, 22F, 23F, and 33F according to the Danish nomenclature.

In another embodiment, the unconjugated vaccine comprises polysaccharides of serotypes 1, 2, 3, 4, 5, 6B, 7F, 8,. 9N, 9V, 10A, 11A, 12F, 14, 15B, 17F, 18C, 19A, 19F, 20, 22F, 23F, and 33F according to the Danish nomenclature dissolved in isotonic saline with 0.25% phenol.

A wide variety of conjugated and unconjugated pneumococcal vaccines may be used in the present invention.

Examples of conjugated vaccines that may be used in the methods of the present invention are:

PCV. This is a heptavalent conjugated pneumococcal vaccine produced by Merck Sharp & Dohme, West Point, Pa., containing capsular polysaccharides of serotypes 4, 6B, 9V, 14, 18C, 19F, and 23F (Danish nomenclature) individually conjugated to the outer membrane protein complex of *Neisseria meningitidis*. Each 0.5 ml dose of PCV contains betweeen 0.1 μg to 5.0 μg of each polysaccharide serotype. PCV is prepared by purifying the above-listed 7 polysaccharides and then conjugating the polysaccharides to the outer membrane protein complex (OMPC) of *Neisseria meningitidis*. Methods of purifying the polysaccharides of PCV are described in European Patent Application EP 0 497 524. Methods of conjugating the purified polysaccharides to OMPC are described in U.S. Pat. No. 4,695,624.

an eleven-valent conjugated pneumococcal vaccine produced by Merck Sharp & Dohme, West Point, Pa., containing capsular polysaccharides of serotypes 1, 3, 4, 5, 6B, 7F, 9V, 14, 18C, 19F, and 23F (Danish nomenclature) individually conjugated to the outer membrane protein complex of *Neisseria meningitidis*. Purification and conjugation of the polysaccharides are as for PCV, above.

a heptavalent pneumococcal conjugate vaccine produced by Lederle Laboratories, Pearl River, N.Y., which contains the capsular polysaccharides of serotypes 4, 6B, 9V, 14, 18C, 19F, and 23F conjugated to the non-toxic CRM197 variant of diptheria toxin.

Examples of unconjugated vaccines that may be used in the methods of the present invention are:

PNEUMOVAX®23. This is a vaccine produced by Merck Sharp & Dohme, West Point, Pa., containing purified capsular polysaccharide antigens from 23 serotypes of *Streptococcus pneumoniae*. Each recommended dose of vaccine (0.5 ml) contains 25 μg of each of 23 type-specific polysaccharides dissolved in isotonic saline. PNEUMOVAX®23 does not contain adjuvant but contains 0.25% phenol as preservative. PNEUMOVAX®23 contains the following 23 serotypes:

| Danish nomenclature | Corresponding American nomenclature | ATCC catalogue number |
|---|---|---|
| 1 | 1 | 15-x |
| 2 | 2 | 16-x |
| 3 | 3 | 17-x |
| 4 | 4 | 18-x |
| 5 | 5 | 57-x |
| 6B | 26 | 58-x |
| 7F | 51 | 27-x |
| 8 | 8 | 20-x |
| 9N | 9 | 21-x |
| 9V | 68 | 59-x |
| 10A | 34 | 60-x |
| 11A | 43 | 61-x |
| 12F | 12 | 22-x |
| 14 | 14 | 23-x |
| 15B | 54 | 62-x |
| 17F | 17 | 63-x |
| 18C | 56 | 28-x |
| 19A | 57 | 64-x |
| 19F | 19 | 24-x |
| 20 | 20 | 65-x |
| 22F | 22 | 66-x |
| 23F | 23 | 25-x |
| 33F | 70 | 67-x |

PNEUMOVAX®23 is described at pages 1768–1770 of the 1997 edition of the Physician's Desk Reference (Medical Economics, Montvale, N.J.). PNEUMOVAX®23 is prepared by a process that involves purifying the above described 23 polysaccharides from *S. pneumoniae*, followed by dissolving the purified polysacchrides in isotonic saline containing 0.25% phenol as a preservative. The purification process for the polysaccharides is described in European Patent Application EP 0 497 524. Alternatively, the 23 polysaccharides of PNEUMOVAX®23 can be obtained from the American Type Culture Collection, where they have the indicated catalogue numbers.

PNU-IMUNE®23. This is an unconjugated pneumococcal polysaccharide vaccine produced by Lederle Laboratories, Pearl River, N.Y., containing the same purified 23 capsular polysaccharide antigens as is contained in PNEUMOVAX®23, described above.

Both the conjugated vaccines and the unconjugated vaccines used in the present invention may contain polysaccharides from any serotype of *Streptococcus pneumoniae*. The number of different serotypes represented in each vaccine may be anywhere from a single serotype to many. For example, PCV contains polysaccharides from 7 different serotypes while PNEUMOVAX®23 contains polysaccharides from 23 different serotypes.

Methods of making unconjugated vaccines that are suitable for use in the present invention using polysaccharides from *S. pneumoniae* are well known in the art. Polysaccharides are first purified from *S. pneumoniae*. The purified polysaccharides can then be dissolved in isotonic saline containing a preservative such as, e.g., 0.25% phenol. The resulting composition can then be used as a vaccine. Methods of purning polysaccharides from *S. pneumoniae* are well known. For example, European Patent Application EP 0 497 524 describes purification methods that are used to produce PNEUMOVAX®23. Additional methods of making unconjugated vaccines that are suitable for use in the present invention are described in, e.g., U.S. Pat. No. 4,686,102; European Patent Application EP 0 002 404.

Methods of making conjugated vaccines that are suitable for use in the present invention using polysaccharides from *S. pneumoniae* are well known in the art. Such methods of conjugating purified polysaccharides from *S. pneumoniae* to OMPC from *Neiserria meningitidis* are described in U.S. Pat. No. 4,695,624 and comprise the steps of:

(a) solubilizing the purified polysaccharide in a non-hydroxylic organic solvent;

(b) activating the polysaccharide with a bifinctional reagent;

(c) reacting the activated polysaccharide with a bis-nucleophile to form a functionalized polysaccharide;

(d) reacting the functionalized polysaccharide with either:
  (i) a reagent generating electrophilic sites to form an electrophilic polysaccharide; or
  (ii) a reagent generating thiol groups to form a thiol polysaccharide;

(e) reacting OMPC with a reagent generating thiol groups to form a thiol OMPC;

(f) reacting OMPC with a reagent generating thiophilic sites to form a thiophilic OMPC;

(g) reacting the electrophilic polysaccharide or the thiol polysaccharide with the thiol OMPC or the thiopbilic OMPC to form a stable covalently bonded conjugate of polysaccharide and OMPC.

Additional methods of making conjugated vaccines that are suitable for use in the present invention are described in, e.g. U.S. Pat. No. 5,371,197; U.S. Pat. No. 4,882,317; U.S. Pat. No. 4,673,574; European Patent Application EP 0 497 524; and International Patent Publication WO 94/04195.

Many methods of analyzing the response to the priming and booster immunizations of the present invention may be used. Generally, some form of antibody assay, such as, e.g., an ELISA, which detects antibodies specific for the various capsular polysaccharides in sera obtained from immunized children, is employed.

There are several methods to measure antibodies to type-specific pneumococcal polysaccharides in the sera of children immunized according to the methods of the present invention. The classic method is the radioimmunoassay (RIA). See, e.g. Schiffiman et al., 1980, J. Immunol. Meth. 33:133–144. The RIA method detects type specific antibodies through incubation of sera with radio-labeled type-specific polysaccharides in suspension. The antigen-antibody complexes are then precipitated with ammonium sulfate and the radiolabeled pellets assayed for counts per minute (cpm).

A newer method is the enzyme-linked immunosorbent assay (ELISA). See, e.g., Koskela & Leinonen, 191981, J. Clin. Pathol. 34:93–98; Kojima et al., 1990, Tohoku J. Exp. Med. 161:209–215. In the ELISA detection method, type-specific antibodies from the sera of vaccinated children are quantitated by incubation with type-specific polysaccharides which have been adhered to polystyrene plates. The bound antibody is detected using secondary detector antibodies. The secondary antibodies have an enzyme covalently attached to them which permits detection with specific substrate, giving a calorimetric readout. Although the RIA was traditionally the preferred assay method, it has some significant disadvantages. It is lengthy, labor intensive, dependent on standard radiolabeled antigen, and expensive. Also, early versions of the RIA did not distinguish between anti-cell wall polysaccharide and anti-type-specific polysaccharide antibodies, although this problem has been corrected. The ELISA is much less labor intensive, appears more sensitive to low antibody levels, and allows isotyping of specific antibodies to determine the isotype contribution, for example, IgM vs. IgG or IgG1 vs. IgG2, in the immune response.

The third option for assessing antibody in serum is the opsonin assay used to measure functional antibodies. Whereas the ELISA and the RIA measure total antigen-specific antibody, the opsonin assay is designed to quantitate only the antibodies which can opsonize the bacteria, thus leading to ingestion and killing of the bacteria. The assay consists of fresh human neutrophils, a source of complement, encapsulated pneumococci, and type specific antisera. The assay readout is the endpoint titer at which 50–75% of the input CFUs (i.e., bacteria) are killed after 2 hours. The biological nature of the assay and its dilution endpoint readout dictate that inter- and intra-assay variation are substantial. It is unlikely that differences between individual samples of less than 8-fold can approach statistical significance. To be comfortable that robust differences are being observed between individual samples, a difference of 10–20-fold may be required. Furthermore, the labor-intensive nature of the assay limits the number of samples that can be processed per run as well as increasing the cost of performing large numbers of assays. Thus, the results of opsonin assays done across multiple serum samples from different individuals are essentially functional antibodies are present than to compare the relative abilities of various vaccines to induce different levels of functional antibodies.

The following non-limiting example is presented to better illustrate the invention.

EXAMPLE

Vaccination Schedule

A total of 119 healthy children from a private pediatric practice in rural Kentucky were vaccinated at age 2 months and again at age 4 months with the conjugated pneumococcal polysaccharide vaccine PCV produced by Merck Sharp & Dohme, West Point, Pa. Vaccinations were given intramuscularly. Each infant received a 0.5 ml dose of PCV per vaccination. This dose contained 2.8 $\mu$g of serotype 6B, 2 $\mu$g of 18C and 19F, and 1 $\mu$g each of 14, 23F, 4, and 9V conjugated to the outer membrane protein complex of *Neisseria meningitidis*.

Of those children, 79 received a third dose of PCV at age 6 months while 40 were immunized with a dose of PNEUMOVAX®23 at the age of 6 months. Each infant received a 0.5 ml dose per vaccination. Each dose of PNEUMOVAX®23 contained 25 $\mu$g of each of the 23 type-specific polysaccharides.

The children also were immunized with various vaccines against non-pneumococcal diseases. At 2 months the children received TETRAMUNE®, ORIMUNE®, and RECOMBIVAX HB®. At 4 months the children received TETRAMUNE® and ORIMUNE®. At 6 months the children received TETRAMUNE®, ORIMUNE®, and RECOMBIVAX HB®. Immunization with such non-pneumococcal vaccines is completely optional and is only reported here for the sake of completeness. The present invention may be practiced with or without such immunizations with non-pneumococcal vaccines.

Results

Blood samples (~3 to 5 ml) were obtained at about age 7 months (i.e., one month after the third immunization) from 73 of the children that received PCV as the third immunization and from 30 of the children that received PNEUMOVAX®23 as the third immunization. Sera were prepared from the blood samples. Geometric Mean Titers (GMTs)

were measured by ELISA for levels of IgG antibodies in the sera to the seven polysaccharide serotypes present in PCV (4, 6B, 9V, 14, 18C, 19F, and 23F). The concentration and volume of coating polysaccharide and the second antibody (alkaline phosphatase-labeled goat anti-human antibody) were optimized independently for each serotype. Pneumococcal C-polysaccharide (CPs) complex was included in the serum diluent in sufficient quantity to adsorb essentially all anti-CPs antibody from the sera.

The ELISAs were run in Corning 96 well flat bottom microtiter plates (Corning #25801). The wells of the microtiter plates were coated with pneumococcal polysaccharide. The following concentrations of polysaccharide were used:

| Polysaccharide Type | Concentration |
| --- | --- |
| 4 | 20 mcg/ml |
| 6B | 10 mcg/ml |
| 9V | 10 mcg/ml |
| 14 | 20 mcg/ml |
| 18C | 25 mcg/ml |
| 19F | 25 mcg/ml |
| 23F | 20 mcg/ml |

The polysaccharides were obtained as dried powders from the Merck Manufacturing Division (or equivalent, e.g., ATCC) and were resuspended in phosphate buffered saline (PBS; 137 mM NaCl, 2.7 mM KCl, 4.3 mM $Na_2HPO_4$, 1.4 mM $KH_2PO_4$, pH 7.2).

For serotypes 6B and 23F, 100 μl of the above polysaccharide dilutions was used per well; for all other serotypes, 50 μl per well was used to coat the wells. The plates were sealed and incubated overnight (13–24 hours) at room temperature on a rocker platform. Following overnight incubation, the wells were washed three times (500 μl per well, 5 second soak/cycle) with PBS+0.05% TWEEN®20. Following the washes, four fold serial dilutions of sera from the immunized children at 7 months were added to the wells. The dilutions were begun at 1:25. The diluent was PBS+ 0.05% TWEEN®20+1.0% bovine serum albumin+10 mcg/ml of pneumococcal C-polysaccharide complex (Statens SerumInstitut, Denmark). Each 7 month serum sample was tested against all 7 polysaccharides. For wells that had been coated with serotypes 6B and 23F, 100 μl of each serum dilution was added per well; for all other serotypes, 50 μl per well was used. Following addition of the serum dilutions, the plates were covered and incubated for two hours at room temperature on a rocker platform. The plates were then washed three times (500 μl per well, 5 second soaktcycle) with PBS+0.05% TWEEN®20.

After these washing steps, labeled secondary antibody (alkaline phosphatase labeled goat anti-human IgG (Kirkegaard and Perry Laboratories, #075-1002) was added. The lyophilized labeled secondary antibody was rehydrated as per the manufacturer's directions in disiled water to prepare a stock solution at a final concentration of 0.5 mg/ml. To prepare a working solution of labeled secondary antibody, this stock solution was diluted 1:1000 in PBS+ 0.05% TWEEN®20. 100 μl of working solution was added to each well that had been coated with serotypes 6B and 23F; for wells that had been coated with other serotypes, 50 μl of working solution per well was added. The plates were then covered and incubated for two hours at room temperature on a rocker platform. Following this incubation, the plates were washed four times (500 μl per well, 5 second soak/cycle) with PBS+0.05% TWEEN®20. Color development was by the addition of 100 μl per well of a solution of 1.0 mg/ml of pnitrophenyl phosphate (Sigma #N2765) in 1.0 M diethanolamine+1 mM $MgCl_2$, pH 9.8. Following addition of p-nitrophenyl phosphate, the plates were incubated at room temperature on a rocker platform until the $OD_{405}$ of the lowest dilution of the standard curve control wells (see below) with polysaccharide was between 1.1 and 2.0. Reactions were stopped with 50 μl of 3M NaOH. Color development was allowed to proceed for the same amount of time in each well. The plates were read on a Titertek MCC340 spectrophotometric plate reader.

As a standard curve, an adult human immune sera sample pool, having IgG concentrations to pnuemococcal polysaccharides as listed below, was used:

| Polysaccharide | IgG to Polysaccharide |
| --- | --- |
| 4 | 21.73 mcg/ml |
| 6B | 21.79 mcg/ml |
| 9V | 18.70 mcg/ml |
| 14 | 50.05 mcg/ml |
| 18C | 20.37 mcg/ml |
| 19F | 11.29 mcg/ml |
| 23F | 24.41 mcg/ml |

As a plate control, i.e., to control for possible variation in results due to plate-to-plate differences in the microtiter plates used, another sample of adult human immune sera was used.

Two fold serial dilutions of these control sera were prepared as follows. The dilutions varied somewhat based upon the polysaccharide type used to coat the wells.

| Polysaccharide | Standard Curve Control Sera | Plate Control Sera |
| --- | --- | --- |
| 4 | 1:500 to 1:8000 | 1:100 to 1:4000 |
| 6B | 1:500 to 1:8000 | 1:250 to 1:1000 |
| 9V | 1:500 to 1:8000 | 1:1000 to 1:4000 |
| 14 | 1:1000 to 1:16000 | 1:2000 to 1:8000 |
| 18C | 1:500 to 1:8000 | 1:1000 to 1:4000 |
| 19F | 1:250 to 1:4000 | 1:1000 to 1:4000 |
| 23F | 1:500 to 1:8000 | 1:500 to 1:2000 |

Dilutions of control sera were assayed as above for the 7 month sera. Based upon results from the controls, a standard curve was constructed, from which the results for the test sera reported in the tables below were obtained.

The results are shown in Table 1. In Table 1, the column heading PCV-PCV-PCV refers to the regimen where the conjugated vaccine PCV was used at ages 2, 4, and 6 months; the column heading PCV-PCV- PNEUMOVAX®23 refers to the regimen where PCV was used at 2 and 4 months and the unconjugated vaccine PNEUMOVAX®23 was used at 6 months. The numbers underneath these column headings report the GMTs for each serotype for the respective vaccination protocols. GMTs are reported in terms of mcg of IgG/ml of sera.

TABLE 1

| Serotype | PCV-PCV-PCV | PCV-PCV- PNEUMOVAX ®23 |
| --- | --- | --- |
| 4 | 0.8 | 1.9 |
| 6B | 0.3 | 0.6 |
| 9V | 1.4 | 2.3 |
| 14 | 2.7 | 4.2 |
| 18C | 0.6 | 1.0 |

TABLE 1-continued

| Serotype | PCV-PCV-PCV | PCV-PCV- PNEUMOVAX ®23 |
|---|---|---|
| 19F | 2.3 | 9.4 |
| 23F | 0.5 | 0.7 |

Table 2 reports these results in terms of the percent increase in GMT that resulted from the 6 month immunization being done with the PNEUMOVAX®23 rather than with the conjugated vaccine PCV.

TABLE 2

| Serotype | Percent Increase |
|---|---|
| 4 | 138% |
| 6B | 100% |
| 9V | 64% |
| 14 | 56% |
| 18C | 67% |
| 19F | 309% |
| 23F | 40% |

It can be seen from Tables 1 and 2 that GMTs for the regimen of immunizing with conjugated vaccine at 2 and 4 months followed by immunizing with unconjugated vaccine at 6 months are higher for every conjugate vaccine serotype.

Adverse Reactions

The frequency of adverse reactions was similar after the 6 month immunization whether the vaccine used was PCV or PNEUMOVAX®23.

The present invention is not to be limited in scope by the specific embodiments described herein. Indeed, various modifications of the invention in addition to those described herein will become apparent to those skilled in the art from the foregoing description. Such modifications are intended to fall within the scope of the appended claims.

Various publications are cited herein, the disclosures of which are incorporated by reference in their entireties.

What is claimed:

1. A method of vaccinating children against *Streptococcus pneumoniae* which comprises:
    (a) immunizing with a conjugated pneumococcal vaccine at the age of about 2 months;
    (b) further immunizing with a conjugated pneumococcal vaccine at the age of about 4 months; and
    (c) further immunizing with an unconjugated pneumococcal vaccine at the age of about 6 months.

2. A method of vaccinating children against *Streptococcus pneumoniae* which comprises:
    (a) immunizing with a conjugated pneumococcal vaccine at the age of 2 months;
    (b) further immunizing with a conjugated pneumococcal vaccine at the age of 4 months; and
    (c) further immunizing with an unconjugated pneumococcal vaccine at the age of 6 months.

3. The method of claim 1 which includes the additional step of:
    (d) further immunizing with an unconjugated pneumococcal vaccine at the age of 12 months.

4. The method of claim 3 where the conjugated vaccine is PCV.

5. The method of claim 3 where the conjugated vaccine comprises polysaccharides of serotypes 4, 6B, 9V, 14, 18C, 19F, and 23F according to the Danish nomenclature.

6. The method of claim 5 where the polysaccharides are conjugated to the outer membrane protein complex of *Neisseria meningitidis*.

7. The method of claim 6 where the conjugated vaccine is produced by a process that comprises the steps of:
    (a) solubilizing the purified polysaccharide in a non-hydroxylic organic solvent;
    (b) activating the polysaccharide with a bifinctional reagent;
    (c) reacting the activated polysaccharide with a bis-nucleophile to form a functionalized polysaccharide;
    (d) reacting the finctionalized polysaccharide with either;
        (i) a reagent generating electrophilic sites to form an electrophilic polysaccharide; or
        (ii) a reagent generating thiol groups to form a thiol polysaccharide;
    (e) reacting the outer membrane protein complex of *Neisseria meningitidis* (OMPC) with a reagent generating thiol groups to form a thiol OMPC;
    (f) reacting OMPC with a reagent generating thiophilic sites to form a thiophilic OMPC;
    (g) reacting the electrophilic polysaccharide or the thiol polysaccharide with the thiol OMPC or the thiophilic OMPC to form a stable covalently bonded conjugate of polysaccharide and OMPC.

8. The method of claim 3 where the conjugated vaccine comprises polysaccharides of serotypes 1, 3, 4, 5, 6B, 7F, 9V, 14, 18C, 19F, and 23F according to the Danish nomenclature.

9. The method of claim 8 where the polysaccharides are conjugated to the outer membrane protein complex of *Neisseria meningitidis*.

10. The method of claim 9 where the conjugated vaccine is produced by a process that comprises the steps of:
    (a) solubilizing the purified polysacchazide in a non-hydroxylic organic solvent;
    (b) activating the polysaccharide with a bifunctional reagent;
    (c) reacting the activated polysaccharide with a bis-nucleophile to form a functionalized polysaccharide;
    (d) reacting the finctionalized polysaccharide with either:
        (i) a reagent generating electrophilic sites to form an electrophilic polysaccharide; or
        (ii) a reagent generating thiol groups to form a thiol polysaccharide;
    (e) reacting the outer membrane protein complex of *Neisseria meningitidis* (OMPC) with a reagent generating thiol groups to form a thiol OMPC;
    (f) reacting OMPC with a reagent generating thiophilic sites to form a thiophilic OMPC;
    (g) reacting the electrophilic polysaccharide or the thiol polysaccharide with the thiol OMPC or the thiophilic OMPC to form a stable covalently bonded conjugate of polysaccharide and OMPC.

11. The method of claim 3 where the conjugated vaccine comprises polysaccharides of serotypes 4, 6B, 9V, 14, 18C, 19F, and 23F conjugated to the non-toxic CRM197 variant of diptheria toxin.

12. The method of claim 3 where the unconjugated vaccine is PNEUMOVAX®23.

13. The method of claim 3 where the unconjugated vaccine comprises polysaccharides of serotypes 1, 2, 3, 4, 5, 6B, 7F, 8, 9N, 9V, 10A, 11A, 12F, 14, 15B, 17F, 18C, 19A, 19F, 20, 22F, 23F, and 33F according to the Danish nomenclature.

14. The method of claim 13 where said polysaccharides are dissolved in isotonic saline with 0.26% phenol.

15. The method of claim 3 where said children are additionally immunized with non-pneumococcal vaccine.

* * * * *